025A

United States Patent [19]

Evanno et al.

[11] Patent Number: 6,075,021

[45] Date of Patent: Jun. 13, 2000

[54] 1H-PYRIDO[3,4-B]INDOLE-4-CARBOXAMIDE DERIVATIVES, PREPARATION AND APPLICATION THEREOF IN THERAPEUTICS

[75] Inventors: Yannick Evanno, Bullion; Mireille Sevrin, Paris; Christian Maloizel, Meudon; Odette Legalloudec, Morigny; Pascal George, Saint Arnoult en Yvelines, all of France

[73] Assignee: Synthelabo, Le Plessis Robinson, France

[21] Appl. No.: 09/284,070

[22] PCT Filed: Oct. 8, 1997

[86] PCT No.: PCT/FR97/01750

§ 371 Date: Apr. 7, 1999

§ 102(e) Date: Apr. 7, 1999

[87] PCT Pub. No.: WO98/15552

PCT Pub. Date: Apr. 16, 1998

[30] Foreign Application Priority Data

Oct. 8, 1996 [FR] France .................... 96 12229

[51] Int. Cl.[7] ............... A61K 31/437; C07D 471/04
[52] U.S. Cl. .............. 514/232.8; 514/253; 514/292; 546/86; 544/126; 544/361
[58] Field of Search ............. 546/86; 544/126, 544/361; 514/232.8, 253, 292

[56] References Cited

FOREIGN PATENT DOCUMENTS 0 96 08490  3/1996  WIPO .

OTHER PUBLICATIONS

C. Herdeis et al., "Synthesis and Serotonin–Receptor Activity of Substituted 1–Oxo–1,2,3,4–tetrahydro–β–carbolines", Zeitschrift Fur Naturforschung, Teil B: Anorganische Chemie, Organische Chemie, vol. 42B, pp. 785–790, (1987).

*Primary Examiner*—Fiona T. Powers
*Attorney, Agent, or Firm*—Finnegan, Henderson, Farabow, Garrett & Dunner, L.L.P.

[57] ABSTRACT

Compounds of general formula (I)

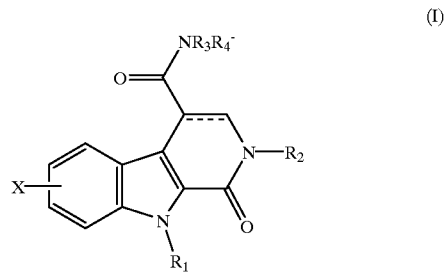

in which the variables are as defined in the specification, their preparation and their application in therapeutics.

15 Claims, No Drawings

1H-PYRIDO[3,4-B]INDOLE-4-CARBOXAMIDE DERIVATIVES, PREPARATION AND APPLICATION THEREOF IN THERAPEUTICS

The subject of the present invention is 1H-pyrido[3,4-b]indole-4-carboxamide derivatives, their preparation and their application in therapeutics.

The compounds of the invention correspond to the general formula (I)

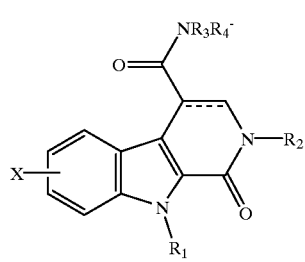

in which
- X represents a hydrogen or halogen atom or a ($C_1$–$C_3$) alkyl, ($C_1$–$C_3$)alkoxy, trifluoromethyl or phenylmethoxy group,
- $R_1$ represents a hydrogen atom or a ($C_1$–$C_3$)alkyl, cyclopropyl or phenylmethyl group,
- $R_2$ represents. either a ($C_1$–$C_3$) alkyl group optionally substituted by a methoxy group, or a phenyl($C_1$–$C_3$) alkyl group optionally substituted on the phenyl ring by a halogen atom or a methyl or methoxy group, or a cyclohexylmethyl group, or a thienylmethyl group, or a pyridinylmethyl group, or a phenyl group optionally substituted by one or more halogen atoms or a ($C_1$–$C_3$) alkyl' or ($C_1$–$C_3$)alkoxy group, or a pyridinyl group, or a 5-methyl-1,2-oxazolyl group, or a 5-methyl-1,3,4-thiadiazolyl group, or a naphthyl group,
- $R_3$ and $R_4$, independently of one another, each represent a hydrogen atom, a ($C_1$–$C_3$)alkyl group, a 2-methoxyethyl group, a hydroxy($C_2$–$C_4$)alkyl group, a carboxy-($C_1$–$C_3$)alkyl group, a ($C_1$–$C_3$)alkoxycarbonyl ($C_1$–$C_3$)alkyl group or a phenyl($C_1$–$C_3$)alkyl group, or else together form, with the nitrogen atom which carries them, either a pyrrolidinyl group optionally substituted by a hydroxyl, ethoxy, methoxycarbonyl or methoxymethyl group, or a piperidinyl group, or a morpholinyl group, or a 4-methylpiperazinyl group, or an azetidinyl group, or a thiazolidinyl group, and the bond between the carbon atoms in the 3 and 4 positions is single or double.

Depending on the nature of this bond, a compound according to the invention can optionally exist in the form of a pure optical isomer or of a mixture of such isomers.

The preferred compounds are those in the general formula of which X is in the 6 position and represents a fluorine atom, $R_1$ represents a methyl group, $R_2$ represents a phenyl group, $R_3$ represents a methyl group and $R_4$ represents an ethyl group or else $R_3$ and $R_4$ form, with the nitrogen atom which carries them, a pyrrolidinyl ring.

The compounds of general formula (I) can be prepared by processes illustrated in the following schemes.

According to Scheme 1, the starting compound corresponds to the general formula (II), in which X is as defined above and $R_1$ is as defined above; when $R_1$ represents hydrogen, it is possible, if desired, to carry out an alkylation in order to produce a compound of general formula (II) in which $R_1$ represents a ($C_1$–$C_3$)alkyl group. The compound of general formula (II) is thus reacted with ethyl pyruvate of formula (III), in acidic medium, for example in the presence of gaseous hydrochloric acid in ethanol or in the presence of sulphuric acid or of boron trifluoride etherate in acetic acid, between room temperature and the reflux temperature, in order to obtain the diester of general formula (IV).

The latter is then treated in ethanol at the reflux temperature with an amine of general formula $R_2NH_2$, in which $R_2$ is as defined above. An ester of general formula (V) is obtained, which is converted to the corresponding acid, of general formula (VI), by hydrolysis in basic medium.

This acid is then converted to the primary, secondary or tertiary amide of general formula (I') by reaction with an amine of general formula $HNR_3R_4$, in which $R_3$ and $R_4$ are as defined above, either through the imidazolide obtained by reaction with N,N'-carbonyldiimidazole or

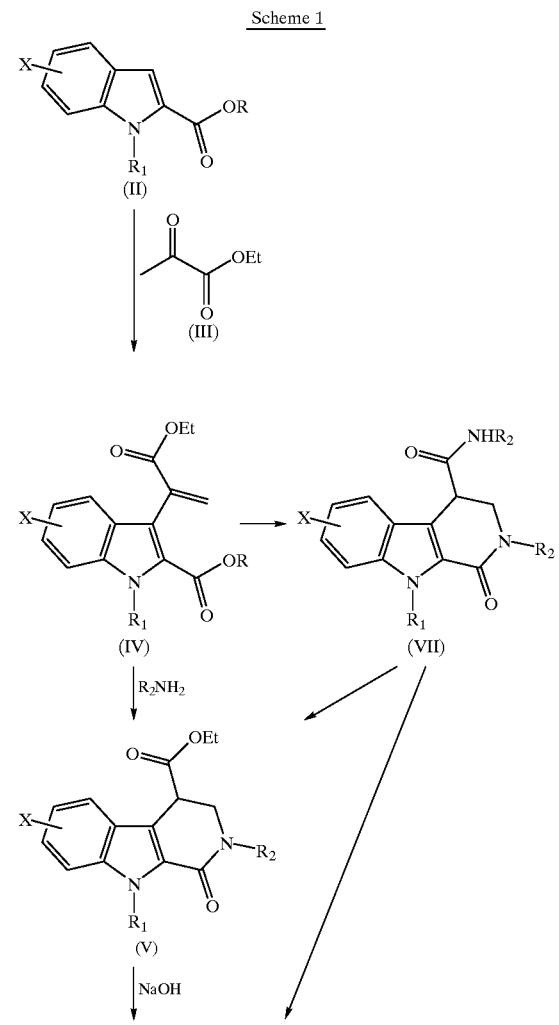

Scheme 1

-continued

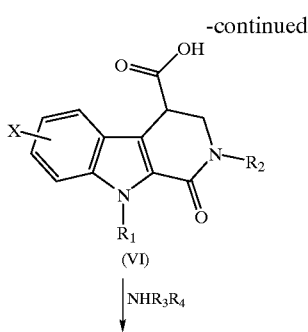

(VI)

↓ NHR₃R₄

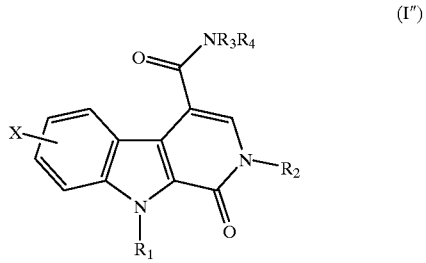

(I')

through the acid chloride.

In the compound of general formula (I') thus obtained, the bond between the 3 and 4 positions is a single bond. If it is desired to prepare a compound in which this bond is a double bond, a compound of general formula (I') is oxidized by means of 2,3-dichloro-5,6-dicyanocyclohexa-2,5-diene-1,4-dione or of 3,4,5,6-tetrachlorocyclohexa-3,5-diene-1,2-dione, in a solvent such as toluene or dichloromethane, between room temperature and the reflux temperature, in order to obtain the corresponding compound, in the structure of which the bond between the carbon atoms in the 3 and 4 positions is double, which respectively has the general formula (I''):

(I'')

Finally, and if it takes place, the enantiomers can be prepared from the racemates according to any known method; thus, for example, an acid of general formula (VI) can be reacted with an optically pure chiral amine, such as α-methylbenzylamine, and the diastereoisomers can be separated by fractional crystallization in order to arrive at an optically pure acid and then at the esters and amides which derive therefrom.

In the case of an optically pure acid of general formula (VI), the non-racemizing coupling reaction can be carried out by any known method, for example with use of (benzotriazol-1-yloxy)tris-(pyrrolidin-1-yl)phosphonium hexafluorophosphate.

In the case where $R_2$ is an aromatic ring, it is possible, if desired, to convert the diester (IV) to the amide (VII) by heating the reaction mixture at a temperature of 100 to 200° C., in an inert solvent or without solvent, for example at reflux of the corresponding amine of general formula $R_2NH_2$. It is then possible to convert the compound of general formula (VII) either to the ester of general formula (V), in refluxing ethanol, in acidic medium, for example in the presence of concentrated hydrochloric acid, or to the acid of general formula (VI), by hydrolysis in basic medium.

The starting compounds of general formula (II), mainly with $R_1$=H, are described in the literature; the pyruvate of formula (III) is commercially available.

According to Scheme 2, the starting compound corresponds to the general formula (VIII), in which X is as defined above. This compound is reacted with 2-ketoglutaric acid and is then treated in an acidic alcoholic medium, for example in ethanol saturated with gaseous hydrochloric acid, at the reflux temperature, in order to obtain the diester of general formula (IX), in which R represents a ($C_1$–$C_3$) alkyl group. If desired, an alkylation reaction of this compound is then carried out, in order to obtain the compound of general formula (X), in which $R_1$ represents a ($C_1$–$C_3$) alkyl group, and then the latter is converted, in a protic solvent, for example N,N-dimethylformamide, in the presence of dimethylformamide dimethyl acetal, at the reflux temperature, in order to obtain the compound of formula (XI). If desired, the compound of general formula (IX) can be directly converted to the compound of general formula (XI), in which $R_1$ represents a methyl group, under the conditions described above.

The compound of general formula (XI) is then treated with an amine of general formula $H_2NR_2$, in which $R_2$ is as defined above, in a protic solvent, for example N,N-dimethylformamide, optionally in the presence of an acid, for example 4-methylbenzenesulphonic acid, at the reflux temperature, in order to obtain the ester of general formula (V'). The latter is converted to the corresponding acid of general formula (VI') by hydrolysis in basic medium.

Finally, this acid is converted to the primary, secondary or tertiary amide of general formula (I''), either through the imidazolide obtained by reaction with N,N'-carbonyldiimidazole or through the acid chloride.

Scheme 2
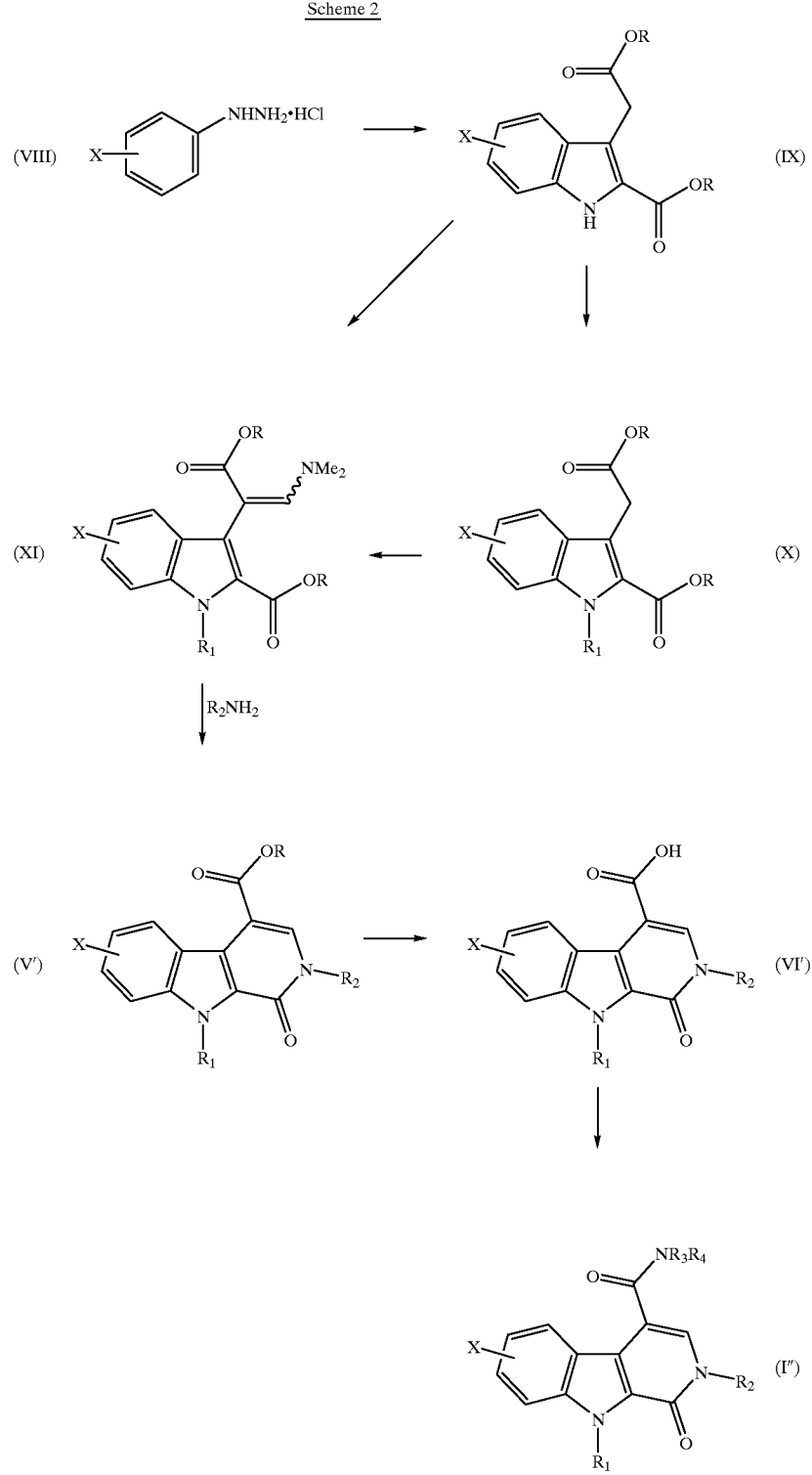

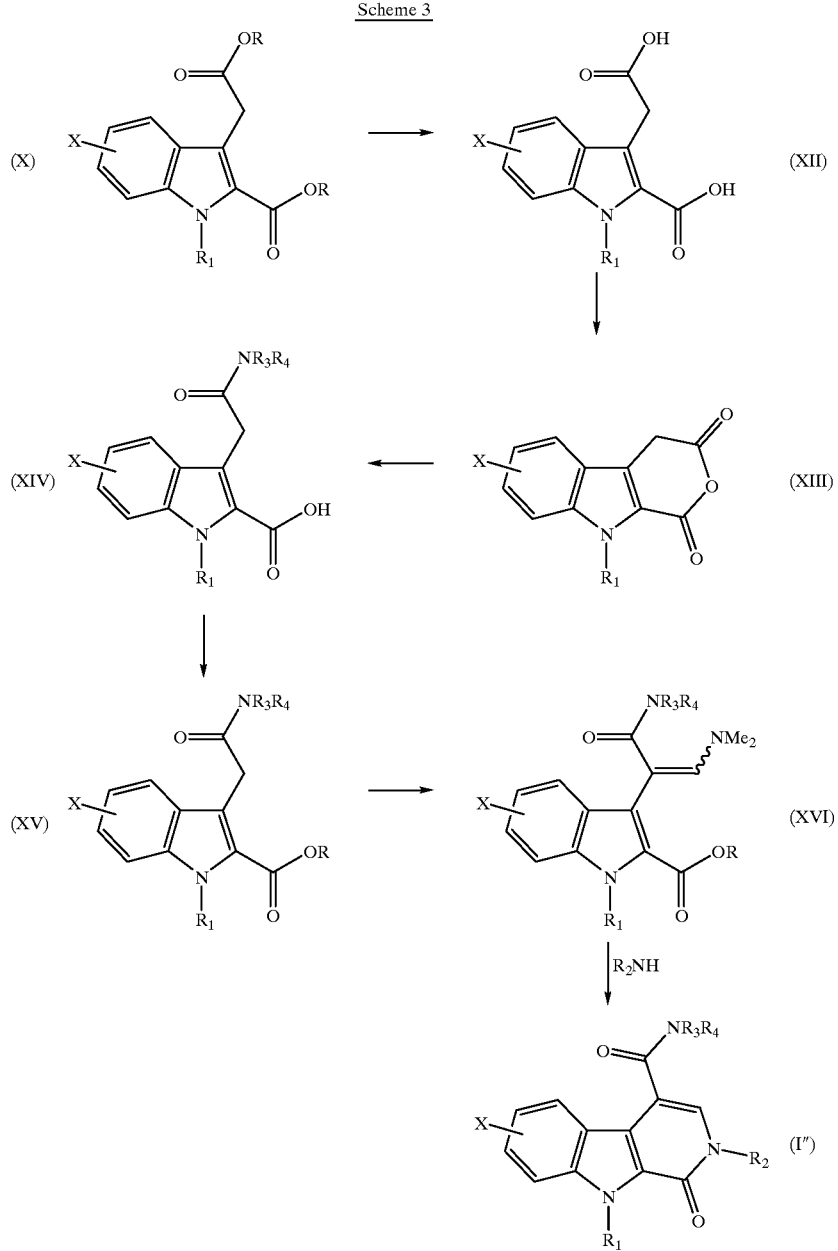

Scheme 3

The starting compounds of general formula (VIII) are commercially available. Some compounds of general formulae (IX) and (X) are described in the literature.

According to Scheme 3, the starting material is the diester of general formula (X), described with respect to the process of Scheme 2. This diester is hydrolysed in acidic medium in order to obtain the diacid of general formula (XII), which is converted to the anhydride, for example by using acetyl chloride at the reflux temperature, in order to obtain the compound of general formula (XIII). The latter is converted, by reaction with an amine of general formula $HNR_3R_4$, in which $R_3$ and $R_4$ are as defined above, in a chlorinated solvent, for example dichloromethane, in order to obtain the compound of general formula (XIV), which is converted to the ester of general formula (XV), the latter is then treated in a protic solvent, for example N,N-dimethylformamide, in the presence of dimethylformamide dimethyl acetal, at the ref lux temperature, in order to obtain the compound of general formula (XVI), and, finally, the latter is reacted with an amine of general formula $R_2NH_2$, in which $R_2$ is as defined above, in a protic solvent, for example N,N-dimethylformamide, optionally in the presence of an acid, for example 4-methylbenzenesulphonic acid, at the reflux temperature, in order to obtain the compound of general formula (I").

Finally, if desired, a secondary amide of general formula (I"), in which $R_3$ or $R_4$ represents hydrogen, can be converted to the tertiary amide by an alkylation reaction known to a person skilled in the art, by means of an alkylating agent, for example an alkyl halide. Likewise, a compound of general formula (I') or (I"), in which $R_1$ represents a hydrogen atom, can be converted to a compound, in the formula of which $R_1$ represents an alkyl group, by an alkylation reaction of known type. Compounds with chemical structures analogous to that of the compounds of the invention are described in CA 83(13) 114712c, CA 94(9) 64698g and CA 96(9) 68779y.

Some compounds of general formulae (XII), (XIII), (XIV) and (XV) are described in the literature. A compound of general formula (I) in which $R_3$ and/or $R_4$ represent a hydroxy($C_2$–$C_4$)alkyl group can be obtained by reaction of the corresponding acid of general formula (VI) or (VI') with an alcohol protected by a conventional protective group, followed by deprotection.

A compound of general formula (I) in which $R_3$ and/or $R_4$ represent a carboxy($C_2$–$C_4$)alkyl group can be obtained by hydrolysis of a corresponding ester. A compound of general formula (I) in which X represents a phenylmethoxy group can be obtained in two stages, known to a person skilled in the art, from a compound of general formula (I) in which X represents a methoxy group.

The following examples illustrate in detail the preparation of a few compounds according to the invention. The elemental microanalyses and the IR and NMR spectra confirm the structures of the compounds obtained.

The numbers of the compounds shown between brackets in the titles correspond to those in the table given below.

EXAMPLE 1 (Compound No. 20)

(±)-6-Fluoro-N,N,9-trimethyl-1-oxo-2-(phenylmethyl)-2,3,4,9-tetrahydro-1H-pyrido[3,4-b]indole-4-carboxamide 1.1. Ethyl 5-fluoro-1-methyl-1H-indole-2-carboxylate.

1.1.1. Ethyl 5-fluoro-1H-indole-2-carboxylate.

150 g (0.92 mol) of 4-fluorophenylhydrazine hydrochloride are added, while cooling the mixture, to a preprepared solution of 23 g (1 mol) of sodium in 1.5 l of methanol and the mixture is stirred at room temperature for 30 min.

The solution is concentrated under reduced pressure, the residue is taken up in dichloromethane and the sodium chloride is separated by filtration. The solvent is evaporated under reduced pressure, the residue is dissolved in 830 ml of ethanol containing 4.4 ml of acetic acid and 102 ml (0.91 mol) of ethyl pyruvate, and the mixture is heated at reflux for 2 h.

The reaction mixture is concentrated under reduced pressure, the residue is taken up in ethyl acetate, the solution is washed with water and dried over sodium sulphate, and the solvent is evaporated under reduced pressure. 181.6 g (0.83 mol) of hydrazone are obtained. 214 g (1.12 mol) of 4-methylbenzenesulphonic acid monohydrate, in solution of 2.5 l of toluene, are dehydrated by heating the reaction mixture for 2 h at reflux in a Dean and Stark apparatus. 181.6 g (0.83 mol) of the hydrazone obtained above are added while cold and the mixture is heated at reflux for 3 h.

The mixture is cooled, ethyl acetate and water are added, the organic phase is separated and dried, and the solvent is evaporated under reduced pressure. The residue is recrystallized from propan-2-ol and the mother liquors are purified by chromatography on a column of silica gel, elution being carried out with dichloromethane. 144 g (0.7 mol) of product are obtained, which product is used as is in the following stage.

1.1.2. Ethyl 5-fluoro-1-methyl-1H-indole-2-carboxylate.

11.7 g (0.39 mol) of sodium hydride, as an 80% suspension in oil, are washed with petroleum ether and then a solution of 62.1 g (0.3 mol) of ethyl 5-fluoro-1H-indole-2-carboxylate in 600 ml of dimethylformamide is added. The mixture is stirred for 2 h at room temperature and then 24.3 ml (0.39 mol) of methyl iodide, in solution in 50 ml of dimethylformamide, are added. The mixture is stirred for 20 h at room temperature and is then poured onto ice-cold water. The reaction mixture is extracted with ethyl acetate, the organic phase is washed and dried over sodium sulphate, the solvent is evaporated under reduced pre'ssure and 62.5 g (0.28 mol) of solid product are obtained, which product is used as is in the following stage.

1.2. Ethyl 2-(ethoxycarbonyl)-5-fluoro-1-methyl-α-methylene-1H-indole-3-acetate.

A solution of 10.5 g (48 mmol) of ethyl 5-fluoro-1-methyl-1H-indole-2-carboxylate, 18 g (155 mmol) of ethyl pyruvate and 7.8 ml of concentrated sulphuric acid in 100 ml of acetic acid is stirred at room temperature for 1 h 30. The mixture is concentrated under reduced pressure, hydrolysis is carried out with ice-cold water, aqueous ammonia is added until the pH is alkaline and extraction is carried out with dichloromethane. The organic phase is washed with water and dried over sodium sulphate, the solvent is evaporated under reduced pressure and the residue is recrystallized from a mixture of pentane and diethyl ether. 13 g (42 mmol) of solid are obtained.

Melting point: 86–88° C.

1.3. Ethyl (±)-6-fluoro-9-methyl-1-oxo-2-(phenylmethyl)-2,3,4,9-tetrahydro-1H-pyrido[3,4-b]indole-4-carboxylate.

A solution of 7 g (23 mmol) of ethyl 2-(ethoxycarbonyl)-5-fluoro-1-methyl-α-methylene-1H-indole-3-acetate and 15 ml (140 mmol) of benzylamine in 200 ml of ethanol is heated at reflux for 8 h. The solvent is evaporated under reduced pressure and the residue is taken up in dichloromethane and 1N hydrochloric acid. The organic phase is washed with water and is dried over sodium sulphate. The solvent is evaporated under reduced pressure and the residue is purified by chromatography on a column of silica gel, elution being carried out with a mixture of dichloromethane and ethyl acetate. 7 g (18 mmol) of solid product are obtained, which product is used as is in the following stage.

1.4. (±)-6-Fluoro-9-methyl-1-oxo-2-(phenylmethyl)-2,3,4,9-tetrahydro-1H-pyrido[3,4-b]indole-4-carboxylic acid.

6 g (16 mmol) of ethyl (±)-6-fluoro-9-methyl-1-oxo-2-(phenylmethyl)-2,3,4,9-tetrahydro-1H-pyrido[3,4-b]indole-4-carboxylate are hydrolysed with 2.5 g of sodium hydroxide in a mixture of water and ethanol, the mixture is concentrated under reduced pressure, water and acetic acid are added, extraction is carried out with ethyl acetate, the organic phase is washed with water and dried over sodium sulphate, and the solvent is evaporated under reduced pressure. 4 g (11 mmol) of solid are obtained, which solid is used as is in the following stage.

Melting point: 264–265° C.

1.5. (±)-6-Fluoro-N,N,9-trimethyl-1-oxo-2-(phenylmethyl)-2,3,4,9-tetrahydro-1H-pyrido[3,4-b]indole-4-carboxamide.

A solution of 4 g (11 mmol) of (±)-6-fluoro-9-methyl-1-oxo-2-(phenylmethyl)-2,3,4,9-tetrahydro-1H-pyrido[3,4-b]indole-4-carboxylic acid and 2.2 g (30 mmol) of 1,1'-carbonyldiimidazole in 200 ml of tetrahydrofuran is heated at 40° C. for 2 h. The reaction mixture is cooled and a large excess of liquefied dimethylamine is added and the mixture is allowed to stir for a few hours.

The solvent is evaporated under reduced pressure, the residue is taken up in dichloromethane and water, the organic phase is separated, washed with water and dried over sodium sulphate, the solvent is evaporated under reduced pressure and the residue is purified by chromatography on a column of silica gel, elution being carried out with a mixture of dichloromethane and methanol. The product is recrystallized from ethyl acetate. 1.2 g (3 mmol) of product are obtained.

Melting point: 185–186° C.

EXAMPLE 2 (Compound No. 59)

6-Fluoro-N,N,9-trimethyl-1-oxo-2-(phenylmethyl)-2,9-dihydro-1H-pyrido[3,4-b]indole-4-carboxamide A solution of 2 g (5 mmol) of (±)-6-fluoro-N,N,9-trimethyl-1-oxo-2-(phenylmethyl)-2,3,4,9-tetrahydro-1H-pyrido[3,4-b]indole-4-carboxamide and of 1.6 g (7 mmol) of 2,3-dichloro-5,6-dicyano-1,4-benzoquinone in 250 ml of dichloromethane is stirred for 1 h. The organic phase is washed and dried over sodium sulphate. The solvent is evaporated under reduced pressure and the residue is purified by chromatography on a column of silica gel, elution being carried out with a mixture of dichloromethane and ethyl acetate. The product is crystallized from diethyl ether. 1 g (2.6 mmol) of product is obtained.

Melting point: 192–193° C.

EXAMPLE 3 (Compound No. 36)

6-Chloro-2-(2-methoxyethyl)-N,N,9-trimethyl-1-oxo-2,3,4,9-tetrahydro-1H-pyrido[3,4-b]indole-4-carboxamide 3.1. Ethyl 5-chloro-1-methyl-1-H-indole-2-carboxylate.

The preparation is carried out as in Example 1.1.2, from 8.95 g (40 mmol) of ethyl 5-chloro-1H-indole-2-carboxylate, 1.6 g (52 mmol) of sodium hydride, as an 80% suspension in oil, and 11.35 g (80 mmol) of methyl iodide. 9.5 g (40 mmol) of solid product are obtained, which product is used as is in the following stage.

3.2. Ethyl 5-chloro-2-(ethoxycarbonyl)-1-methyl-α-methylene-1H-indole-3-acetate.

A solution saturated with hydrochloric acid and containing 9.5 g (40 mmol) of ethyl 5-chloro-1-methyl-1H-indole-2-carboxylate and 8.8 ml (80 mmol) of ethyl pyruvate is heated at reflux for 4 h. The solvent is evaporated under reduced pressure, the residue is taken up in ethyl acetate, which is washed to neutrality, the organic phase is dried over sodium sulphate and the solvent is evaporated under reduced pressure. The product is purified by chromatography on a column of silica gel, elution being carried out with dichloromethane. 9.6 g (32 mmol) of solid product are obtained, which product is used as is in the following stage.

3.3. Ethyl (±)-6-chloro-2-(2-methoxyethyl)-9-methyl-1-oxo-2,3,4,9-tetrahydro-1H-pyrido[3,4-b]indole-4-carboxylate.

A solution of 9.5 g (31 mmol) of ethyl 5-chloro-2-(ethoxycarbonyl)-1-methyl-α-methylene-1H-indole-3-acetate and 8.1 g (93 mmol) of 2-methoxyethylamine in 20 ml of ethanol is heated at reflux for 3 h.

The solvent is evaporated under reduced pressure and the residue is taken up in ethyl acetate, which is washed with water and dried over sodium sulphate. 9.7 g (27 mmol) of solid product are obtained, which product is used as is in the following stage.

3.4. (±)-6-Chloro-2-(2-methoxyethyl)-9-methyl-1-oxo-2,3,4,9-tetrahydro-1H-pyrido[3,4-b]indole-4-carboxylic acid.

9.6 g (26 mmol) of ethyl (±)-6-chloro-2-(2-methoxyethyl)-9-methyl-1-oxo-2,3,4,9-tetrahydro-1H-pyrido[3,4-b]indole-4-carboxylate are hydrolysed with a solution of 3.1 g (80 umol) of sodium hydroxide in 260 ml of ethanol and 50 ml of water. The reaction mixture is concentrated, the residue is taken up in water and the aqueous phase is washed with ethyl acetate and acidified to pH=1 with concentrated hydrochloric acid. Extraction is carried out with ethyl acetate. The organic phase is washed with water and dried with sodium sulphate. The solvent is evaporated under reduced pressure and 8.3 g (26 mmol) of solid product are obtained, which product is used as is in the following stage.

3.5. (±)-6-Chloro-2-(2-methoxyethyl)-N,N,9-trimethyl-1-oxo-2,3,4,9-tetrahydro-1H-pyrido[3,4-b]indole-4-carboxamide.

The preparation is carried out as in Example 1.5, from 8.3 g (26 mmol) of (±)-6-chloro-2-(2-methoxyethyl)-9-methyl-1-oxo-2,3,4,9-tetrahydro-1H-pyrido[3,4-b]indole-4-carboxylic acid and from dimethylamine. 8.6 g of product are isolated, which product is recrystallized from propan-2-ol. 6.9 g (19 mmol) of product are obtained.

Melting point: 217–219° C.

EXAMPLE 4 (Compound No. 77)

(+)-6-Fluoro-N,N,9-trimethyl-1-oxo-2-(phenylmethyl)-2,3,4,9-tetrahydro-1H-pyrido[3,4-b]indole-4-carboxamide 4.1. (+)-6-Fluoro-9-methyl-1-oxo-2-(phenylmethyl)-2,3,4,9-tetrahydro-1H-pyrido[3,4-b]indole-4-carboxylic acid.

A solution of 20.5 g (58 mmol) of (±)-6-fluoro-9-methyl-1-oxo-2-(phenylmethyl)-2,3,4,9-tetrahydro-1H-pyrido[3,4-b]indole-4-carboxylic acid and of 7.5 ml (58 mmol) of (R)-(+)-α-methylbenzylamine in 1000 ml of methanol is stirred. The mixture is concentrated under reduced pressure, the residue is taken up in 50 ml of ethyl acetate and 400 ml of diethyl ether, and the precipitate is separated by filtration and recrystallized three times from propan-2-ol.

7.3 g (15 mmol) of diastereoisomer salt are isolated, which salt is redissolved in 100 ml of methanol, 16 ml of 1N hydrochloric acid and 200 ml of water are added, and the precipitate is separated by filtration and dried under reduced pressure at room temperature. 5.1 g (15 mmol) of dextrorotatory acid are obtained.

Melting point: 264–269° C. $[\alpha]_D^{20}$=+41.6° (c=0.5, $CH_3OH$) ee>99% (HPLC).

4.2. (+)-6-Fluoro-N,N,9-trimethyl-1-oxo-2-(phenylmethyl)-2,3,4,9-tetrahydro-1H-pyrido[3,4-b]indole-4-carboxamide.

A solution of 0.5 g (1.3 mmol) of (+)-6-fluoro-9-methyl-1-oxo-2-(phenylmethyl)-2,3,4,9-tetrahydro-1H-pyrido[3,4-b]indole-4-carboxylic acid, 0.11 g (1.3 mmol) of dimethylamine hydrochloride, dried beforehand under reduced pressure, and 0.68 g (13 mmol) of (benzotriazol-1-yloxy)tris(pyrrolidino)phosphonium hexafluorophosphate in 10 ml of dichloromethane, passed beforehand through an alumina column, is cooled to −30° C. and 0.68 ml (3.9 mmol) of N,N-di(1-methylethyl)ethylamine, in solution in 5 ml of dichloromethane, is added dropwise. The mixture is stirred for 6 h at between −30° C. and −20° C., hydrolysis is carried out with 10 ml of 5% aqueous potassium hydrogensulphate solution, the mixture is extracted with dichloromethane, the organic phase is washed and dried, the solvent is evaporated under reduced pressure, the residue is purified by chromatography on a column of silica gel, elution being carried out with a mixture of dichloromethane and ethyl acetate, and the product obtained is recrystallized from propan-2-ol. 0.37 g (1 mmol) of dextrorotatory amide is obtained.

Melting point: 199–202° C. $[\alpha]_D^{20}=+6.3°$ (c 1, $CHCl_3$) ee>94% (HPLC).

EXAMPLE 5 (Compound No. 76)

(−)-6-Fluoro-N,N,9-trimethyl-1-oxo-2-(phenylmethyl)-2,3,4,9-tetrahydro-1H-pyrido[3,4-b]indole-4-carboxamide 5.1. (−)-6-Fluoro-9-methyl-1-oxo-2-(phenylmethyl)-2,3,4,9-tetrahydro-1H-pyrido[3,4-b]indole-4-carboxylic acid.

The solvent from the various mother liquors from the recrystallization of the diastereoisomer salt of Example 4.1 is evaporated under reduced pressure, water and concentrated hydrochloric acid are added, and the precipitate is separated by filtration and dried under reduced pressure at room temperature. 13.6 g (38 mmol) of impure laevorotatory acid are obtained, to which are added 250 ml of methanol and 4.97 ml (38 mmol) of (S)-(−)-α-methylbenzylamine.

The mixture is stirred and concentrated under reduced pressure and the precipitate is collected by filtration and recrystallized three times from propan-2-ol. 7 g (15 mmol) of diastereoisomer salt are obtained, which salt is redissolved in the minimum amount of methanol, 15 ml of 1N hydrochloric acid are added and the volume of the solution is doubled with water. The precipitate is separated by filtration, washed with water, superficially dried, and dried at room temperature under reduced pressure. 5 g (14 mmol) of laevorotatory acid are obtained.

Melting point: 264–269° C. $[\alpha]_D^{20}=-42.2°$ (c=0.5, $CH_3OH$) ee>99% (HPLC).

5.2. (−)-6-Fluoro-N,N,9-trimethyl-1-oxo-2-(phenylmethyl)-2,3,4,9-tetrahydro-1H-pyrido[3,4-b]indole-4-carboxamide.

By carrying out the preparation as described in Example 4.2, from (−)-6-fluoro-9-methyl-1-oxo-2-(phenylmethyl)-2,3,4,9-tetrahydro-1H-pyrido[3,4-b]indole-4-carboxylic acid and from dimethylamine, 0.3 g (0.8 mmol) of laevorotatory amide is obtained after final recrystallization from ethyl acetate.

Melting point: 204–205° C. $[\alpha]_D^{20}=-7.5°$ (c=1, $CHCl_3$) ee>98% (HPLC).

EXAMPLE 6 (Compound No. 101)

6-Fluoro-N,N, 9-trimethyl-1-oxo-2-phenyl-2,9-dihydro-1H-pyrido[3,4-b]indole-4-carboxamide 6.1. Ethyl 2-(ethoxycarbonyl)-5-fluoro-α-methylene-1H-indole-3-acetate.

A solution of 37.2 g (180 mmol) of ethyl 5-fluoro-1H-indole-2-carboxylate, 25.8 g (222 mmol) of ethyl pyruvate and 31 ml of concentrated sulphuric acid in 400 ml of acetic acid is stirred for 20 h.

The solvent is evaporated under reduced pressure, the residue is taken up in water and ethyl acetate, the organic phase is separated, washed with a dilute aqueous ammonia solution and then with a saturated aqueous sodium chloride solution and dried over sodium sulphate, and the solvent is evaporated under reduced pressure.

37.1 g (122 mmol) of solid product are obtained, which product is used as is in the following stage.

6.2. 6-Fluoro-1-oxo-2-phenyl-2,3,4,9-tetrahydro-1H-pyrido[3,4-b]indole-4-carboxylic acid.

A mixture of 25 g (82 mmol) of ethyl 2-(ethoxycarbonyl)-5-fluoro-α-methylene-1H-indole-3-acetate and 31.8 g (342 mmol) of aniline is heated at reflux for 17 h. A dilute hydrochloric acid solution and ethyl acetate are added, the organic phase is separated, washed with water and dried with sodium sulphate, and the solvent is evaporated under reduced pressure. 30 g of residue are obtained, which residue is hydrolysed with a solution of 43 ml of 30% sodium hydroxide in 400 ml of ethanol at reflux for 1 h.

The mixture is concentrated under reduced pressure, water is added, the mixture is washed with ethyl acetate and dichloromethane, the aqueous phase is acidified with concentrated hydrochloric acid, and the precipitate is collected by filtration and dried under reduced pressure.

18.5 g (57 mmol) of solid compound are obtained, which compound is used as is in the following stage.

6.3. 6-Fluoro-N,N,9-trimethyl-1-oxo-2-phenyl-2,9-dihydro-1H-pyrido[3,4-b]indole-4-carboxamide.

5 g (15 mmol) of 6-fluoro-1-oxo-2-phenyl-2,3,4,9-tetrahydro-1H-pyrido[3,4-b]indole-4-carboxylic acid in 40 ml of thionyl chloride are heated at reflux for 1 h. The solvent is evaporated under reduced pressure, the residue is taken up in dichloromethane, a large excess of liquefied dimethylamine is added, the mixture is stirred for a few hours, water is added, and the precipitate is separated by filtration and dried under reduced pressure.

3.4 g (9 mmol) of compound are obtained.

2.5 g thereof are dissolved in 50 ml of dimethyl sulphoxide, 0.6 g of powdered potassium hydroxide and 1.2 ml of iodomethane are added, and the mixture is stirred for 5 h at 50° C. and then for 20 h at room temperature.

Dilute hydrochloric acid is added, extraction is carried out with ethyl acetate, the organic phase is dried over sodium sulphate, the solvent is evaporated under reduced pressure and the residue is purified by chromatography on a column of silica gel, elution being carried out with a mixture of cyclohexane and ethyl acetate.

2.2 g of a mixture containing 6-fluoro-N,N,9-trimethyl-1-oxo-2-phenyl-2,9-dihydro-1H-pyrido[3,4-b]indole-4-carboxamide and 6-fluoro-N,N,9-trimethyl-1-oxo-2-phenyl-2,3,4,9-tetrahydro-1H-pyrido[3,4-b]indole-4-carboxamide are obtained.

This mixture is stirred with 1 g of 2,3-dichloro-5,6-dicyano-1,4-benzoquinone for 20 h and is washed with a saturated aqueous sodium hydrogencarbonate solution, the organic phase is separated and dried over sodium sulphate, the solvent is evaporated under reduced pressure, the residue is purified by chromatography on a column of silica gel, elution being carried out with a mixture of cyclohexane and ethyl acetate, and the product is recrystallized from ethyl acetate. 0.5 g (1.5 mmol) of compound is obtained.

Melting point: 195–197° C.

EXAMPLE 7 (Compound No. 97)

N,N,9-Trimethyl-1-oxo-2-phenyl-2,3,4,9-tetrahydro-1H-pyrido[3,4-b]indole-4-carboxamide 7.1. Ethyl 2-(ethoxycarbonyl)-α-methylene-1H-indole-3-acetate An ethanol solution saturated with gaseous hydrochloric acid containing 39.1 g (207 mmol) of ethyl 1H-indole-2-carboxylate and 45.3 ml (410 umol) of ethyl pyruvate is brought to approximately 60° C. for 3 h. The mixture is concentrated under reduced pressure and the residue is taken up in diethyl ether. The organic phase is washed with water and dried over sodium sulphate. The solvent is evaporated under reduced pressure and the residue is crystallized from cyclohexane. 45.4 g (158 mmol) of solid product are obtained, which product is used as is in the following stage.

7.2. 1-Oxo-N,2-diphenyl-2,3,4,9-tetrahydro-1H-pyrido[3,4-b]indole-4-carboxamide.

A mixture of 32 g (111 mmol) of ethyl 2-(ethoxycarbonyl)-α-methylene-1H-indole-3-acetate and of 47.5 g (511 mmol) of aniline is heated at reflux for 13 h. Dichloromethane is added and the organic phase is washed with 1N hydrochloric acid. It is dried over sodium oulphate and the solvent is evaporated under reduced pressure. 38.8 g of impure product are obtained, which product is used as is in the following stage.

7.3. Ethyl 1-oxo-2-phenyl-2,3,4,9-tetrahydro-1H-pyrido[3,4-b]indole-4-carboxylate.

A solution of 38.8 g of impure 1-oxo-N,2-diphenyl-2,3,4,9-tetrahydro-1H-pyrido[3,4-b]indole-4-carboxamide in a mixture of ethanol, water and 37% hydrochloric acid is heated at reflux for 8 h.

The reaction mixture is neutralized with concentrated sodium hydroxide and extraction is carried out with ethyl acetate. The organic phase is dried over sodium sulphate and evaporated under reduced pressure. The residue is purified by chromatography on a column of silica gel, elution being carried out with a mixture of dichloromethane and ethyl acetate. 22.6 g (68 mmol) of product are obtained, which product is used as is in the following stage.

7.4. 1-Oxo-2-phenyl-2,3,4,9-tetrahydro-1H-pyrido[3,4-b]indole-4-carboxylic acid.

22.6 g (68 mmol) of ethyl 1-oxo-2-phenyl-2,3,4,9-tetrahydro-1H-pyrido[3,4-b]indole-4-carboxylate are hydrolysed with 200 ml of 1N sodium hydroxide in 500 ml of methanol. The reaction mixture is acidified with 1N hydrochloric acid and the precipitate is filtered off. It is dried under reduced pressure. 18.1 g (59 mmol) of solid product are obtained, which product is used as is in the following stage.

7.5. N,N-Dimethyl-1-oxo-2-phenyl-2,3,4,9-tetrahydro-1H-pyrido[3,4-b]indole-4-carboxamide.

A solution of 10 g (33 mmol) of 1-oxo-2-phenyl-2,3,4,9-tetrahydro-1H-pyrido[3,4-b]indole-4-carboxylic acid in 30 ml of thionyl chloride is heated at reflux for 4 h. The solvent is evaporated under reduced pressure, the residue is taken up in dichloromethane and a large excess of liquefied dimethylamine is added. The mixture is stirred for several hours and the solvent is evaporated under reduced pressure. Water and ethyl acetate are added.

The precipitate is filtered off and dried under reduced pressure. 8.2 g of impure product are obtained, which product is used as is in the following stage.

7.6. N,N,9-Trimethyl-1-oxo-2-phenyl-2,3,4,9-tetrahydro-1H-pyrido[3,4-b]indole-4-carboxamide A mixture of 1.3 g (23 mmol) of powdered potassium hydroxide and of 6 g of impure N,N-dimethyl-1-oxo-2-phenyl-2,3,4,9-tetrahydro-1H-pyrido[3,4-b]indole-4-carboxamide in 60 ml of dimethyl sulphoxide is heated at 40° C. for 30 min. 2.5 ml (40 mmol) of iodomethane are added and the reaction mixture is stirred for 5 h at room temperature.

Water and dichloromethane are then added. The organic phase is dried over sodium sulphate and evaporated under reduced pressure. The residue is purified by chromatography on a column of silica gel, elution being carried out with a mixture of dichloromethane and ethyl acetate. The product is recrystallized from ethyl acetate. 1.9 g (5.5 mmol) of product are obtained.

Melting point: 196–197° C.

EXAMPLE 8 (Compound No. 123)

N-Ethyl-6-fluoro-N,9-dimethyl-1-oxo-2-phenyl-2,9-dihydro-1H-pyrido[3,4-b]indole-4-carboxamide 8.1. Ethyl 2-(ethoxycarbonyl)-5-fluoro-1H-indole-3-acetate A solution of 7.4 g (185 mmol) of sodium hydroxide in 75 ml of water is added to a solution of 30 g (185 mmol) of 4-fluorophenylhydrazine hydrochloride in 300 ml of water, the mixture is stirred for 15 min and then a solution of 29 g (198 mmol) of ketoglutaric acid in 60 ml of water is added. The reaction mixture is stirred at room temperature for 3 h and is extracted with ethyl acetate, and the organic phase is washed with water, dried over sodium sulphate and evaporated under reduced pressure. 42 g (144 mmol) of product are obtained, which product is dissolved in 420 ml of ethanol saturated with gaseous hydrochloric acid and heated at reflux for 4 h.

The reaction mixture is concentrated under reduced pressure, the residue is taken up in ethyl acetate, and the organic phase is washed with normal sodium hydroxide and then with water, dried over magnesium sulphate and evaporated under reduced pressure. 42 g (143 mmol) of solid product are obtained, which product is used as is in the following stage.

8.2. Ethyl 2-(ethoxycarbonyl)-5-fluoro-1-methyl-1H-indole-3-acetate.

A solution of 7.36 g (184 mmol) of 60% sodium hydride, washed beforehand with petroleum ether, and 45 g (153 mmol) of ethyl 2-(ethoxycarbonyl)-5-fluoro-1H-indole-3-acetate in 450 ml of N,N-dimethylformamide is stirred for 2 h at room temperature and then a solution of 19 ml (306 mmol) of iodomethane in 100 ml of N,N-dimdthylformamide is added. After stirring for 20 h, the reaction mixture is poured onto ice-cold water, extraction is carried out with diethyl ether, the organic phase is washed with water and dried over magnesium oulphate, and the solvent is evaporated under reduced pressure. 44.3 g (144 mmol) of product are obtained, which product is used as is in the following stage.

8.3. Ethyl α-(dimethylaminomethylidene)-2-(ethoxycarbonyl)-5-fluoro-1-methyl-1H-indole-3-acetate.

A solution of 44.3 g (144 mmol) of ethyl 2-(ethoxycarbonyl)-5-fluoro-1-methyl-1H-indole-3-acetate and 57.4 ml of dimethylformamide dimethyl acetal in 450 ml of N,N-dimethylformamide is heated at reflux for 50 h. The solvent is evaporated under reduced pressure and the residue is taken up in diethyl ether. The insoluble material is removed by filtration and the solvent is concentrated under reduced pressure. 49.3 g (136 mmol) of solid product are obtained, which product is used as is in the following stage.

8.4. Ethyl 6-fluoro-9-methyl-1-oxo-2-phenyl-2,9-dihydro-1H-pyrido[3,4-b]indole-4-carboxylate.

A solution of 16.3 g (45 mmol) of ethyl α-(dimethylaminomethylidene)-2-(ethoxycarbonyl)-5-fluoro-1-methyl-1H-indole-3-acetate, 4.64 ml (50 mmol) of aniline and 1.6 g (8 mmol) of 4-methylbenzene-sulphonic acid monohydrate in 160 ml of N,N-dimethylformamide is heated at reflux for 24 h. 3.3 g (31 mmol) of sodium carbonate are added in small portions and reflux is continued for 2 h.

The solution is cooled and poured onto ice-cold water. Extraction is carried out with ethyl acetate and the organic phase is washed with water, dried over magnesium sulphate and evaporated under reduced pressure. The residue is purified by chromatography on a column of silica gel, elution being carried out with a mixture of dichloromethane and ethyl acetate. 10.9 g (30 mmol) of product are obtained, which product is used as is in the following stage.

8.5. 6-Fluoro-9-methyl-1-oxo-2-phenyl-2,9-dihydro-1H-pyrido[3,4-b]indole-4-carboxylic acid.

A solution of 22.8 g (65 mmol) of ethyl 6-fluoro-9-methyl-1-oxo-2-phenyl-2,9-dihydro-1H-pyrido[3,4-b]indole-4-carboxylate and of 7.46 g (186 mmol) of sodium hydroxide in a mixture of 1 l of ethanol and 100 ml of water is heated at reflux for 3 h. The mixture is concentrated under reduced pressure, the residue is taken up in water and the aqueous phase is washed with ethyl acetate. Acidification is carried out with concentrated hydrochloric acid to pH=1 and the product is filtered off, which product is rinsed several times with water. It is dried under reduced pressure. 20.4 g (64 mmol) of solid compound are obtained, which compound is used as is in the following stage.

8.6. 6-Fluoro-N,9-dimethyl-1-oxo-2-phenyl-2,9-dihydro-1H-pyrido[3,4-b]indole-4-carboxamide.

A solution of 5 g (15.6 mmol) of 6-fluoro- 9-methyl-1-oxo-2-phenyl-2,9-dihydro-1H-pyrido[3,4-b]-indole-4-carboxylic acid and of 4.8 g (30 mmol) of N,N'-carbonyldiimidazole in 100 ml of N,N-dimethylformamide is stirred at 60° C. for 4 h. A large excess of liquefied methylamine is added at room temperature and the reaction mixture is stirred for 20 h. The solution is poured onto ice-cold water and the precipitate is collected by filtration, washed with a saturated sodium hydrogencarbonate solution, with water and then with ethyl acetate, and dried under reduced pressure. 3.5 g of crude product are isolated. The filtrates are combined and extracted with dichloromethane. The organic phase is washed with a sodium hydrogencarbonate solution and then with water and dried over magnesium sulphate, and the solvent is evaporated under reduced pressure. 1.5 g of additional product are isolated. The two batches are combined and purified by chromatography on a column of silica gel, elution being carried out with a mixture of dichloromethane and ethyl acetate. 4.7 g (13.5 mmol) of solid product are obtained.

8.7. N-Ethyl-6-fluoro-N,9-dimethyl-1-oxo-2-phenyl-2,9-dihydro-1H-pyrido[3,4-b]indole-4-carboxamide.

A solution of 2.5 g (7.1 zmol) of 6-fluoro-N,9-dimethyl-1-oxo-2-phenyl-2,9-dihydro-1H-pyrido[3,4-b]indole-4-carboxamide and of 0.36 g (9 mmol) of 60% sodium hydride, washed beforehand with petroleum ether, is stirred for 3 h at 50° C. 1.67 ml (21 mmol) of iodoethane are added, stirring is maintained for 20 h, and the solution is poured onto ice-cold water and extracted with ethyl acetate. The organic phase is washed with water, dried over magnesium sulphate and evaporated under reduced pressure. The residue is purified by chromatography on silica, the elution being carried out with a mixture of dichloromethane and ethyl acetate. The product is recrystallized from propan-2-ol. 2.3 g of solid are obtained.

Melting point: 181–182° C.

EXAMPLE 9 (Compound No. 98)

6-Fluoro-9-methyl-2-phenyl-4-(pyrrolidin-1-ylcarbonyl)-2,9-dihydro-1H-pyrido[3,4-b]indol-1-one A solution of 3.2 g (10 mmol) of 6-fluoro-9-methyl-1-oxo-2-phenyl-2,9-dihydro-1H-pyrido[3,4-b]indole-4-carboxylic acid and of 3.2 g (20 mmol) of N,N'-carbonyldiimidazole in 65 ml of N,N-dimethylformamide is stirred for 4 h at 60° C. 2.5 ml (30 zmol) of pyrrolidine are added at room temperature and the reaction mixture is stirred for 20 h.

The solution is poured onto ice-cold water and extracted with ethyl acetate. The organic phase is washed with water and dried over magnesium sulphate, and the solvent is evaporated under reduced pressure. The residue is purified by chromatography on a column of silica gel, elution being carried out with a mixture of dichloromethane and ethyl acetate. The product is recrystallized from propan-2-ol. 3 g (7.7 mmol) of solid are obtained.

Melting point: 203–205° C.

EXAMPLE 10 (Compound No. 122)

6-Fluoro-N,N,9-trimethyl-1-oxo-2-(pyridin-2-yl)-2,9-dihydro-1H-pyrido[3,4-b]indole-4-carboxamide 10.1. Methyl 6-fluoro-9-methyl-1-oxo-2-(pyridin-2-yl)-2,9-dihydro-1H-pyrido[3,4-b]indole-4-carboxylate.

A mixture of 4.1 g (12.2 mmol) of methyl α-(dimethylaminomethylidene)-5-fluoro-2-(methoxycarbonyl)-1-methyl-1H-indole-3-acetate and of 1.73 g (18.4 mmol) of 2-aminopyridine is heated at 180° C. for 30 min. 7 ml of N,N-dimethylformamide are added and heating is continued for 4 h.

The reaction mixture is cooled and poured onto a mixture of water and ethyl acetate, and the insoluble material is collected by filtration and dried under reduced pressure. 1.8 g (5.1 mmol) of solid are obtained, which solid is used as is in the following stage.

10.2. 6-Fluoro-9-methyl-1-oxo-2-(pyridin-2-yl)-2,9-dihydro-1H-pyrido[3,4-b]indole-4-carboxylic acid.

A solution of 3.3 g (9.4 mmol) of methyl 6-fluoro-9-methyl-1-oxo-2-(pyridin-2-yl)-2,9-dihydro- 1H-pyrido[3,4-b]indole-4-carboxylate in a mixture of 100 ml of ethanol and of 28 ml of 1N sodium hydroxide is heated at reflux for 4 h. The mixture is concentrated under reduced pressure, water is added, acidification is carried out with concentrated hydrochloric acid and the precipitate is collected by filtration. It is washed with water and dried under reduced pressure. 2.8 g (8.3 mmol) of solid product are obtained, which product is used as is in the following stage.

10.3. 6-Fluoro-N,N,9-trimethyl-1-oxo-2-(pyridin-2-yl)-2,9-dihydro-1H-pyrido[3,4-b]indole-4-carboxamide.

A solution of 2.5 g (7.4 mmol) of 6-fluoro-9-methyl-1-oxo-2-(pyridin-2-yl)-2,9-dihydro-1H-pyrido[3,4-b]indole- 4-carboxylic acid and of 2.4 g (14.8 mmol) of N,N'-carbonyldiimidazole in 65 ml of N,N-dimethylformamide is stirred for 4 h. The reaction mixture is cooled and a large excess of liquefied dimethylamine is added. The mixture is stirred for 48 h at room temperature, poured into water and extracted with ethyl acetate. The organic phase is washed with water and dried over magnesium sulphate, and the solvent is evaporated under reduced pressure. The residue is purified by chromatography on a column of silica gel, elution being carried out with a mixture of dichloromethane and ethyl acetate. The product is recrystallized from ethyl acetate.

1.6 g (4.4 mmol) of solid are obtained.

Melting point: 220–221° C.

EXAMPLE 11 (Compound No. 125)

6-Fluoro-9-methyl-2-(5-methyl-1,3,4-thiadiazol-2-yl)-4-(pyrrolidin-1-ylcarbonyl)-2,9-dihydro-1H-pyrido[3,4-b]indol-1-one 11.1. 2-Carboxy-5-fluoro-1H-indole-3-acetic acid.

A solution of 26.5 g (103 mmol) of ethyl 2-(ethoxycarbonyl)-5-fluoro-1H-indole-3-acetate and 24 g of sodium hydroxide in a mixture of 530 ml of ethanol and of 100 ml of water is heated at reflux. The mixture is concentrated under reduced pressure, water is added, and the aqueous phase is washed with ethyl acetate and acidified with concentrated hydrochloric acid. The precipitate is filtered off, rinsed with water and dried under reduced pressure. 23.4 g (98.7 mmol) of product are obtained, which product is used as is in the following stage.

11.2. 6-Fluoro-1,3,4,9-tetrahydropyrano[3,4-b]-indole-1,3-dione.

A solution of 4.7 g (19.8 mmol) of 2-carboxy-5-fluoro-1H-indole-3-acetic acid in 94 ml of acetyl chloride is heated at reflux for 5 h. The mixture is concentrated under reduced pressure, toluene is added and the solvents are evaporated under reduced pressure. 4.5 g of solid product are obtained, which product is used as in the following stage.

11.3. 5-Fluoro-3-(2-oxo-2-(pyrrolidin-1-yl)ethyl)-1H-indole-2-carboxylic acid.

A solution of 4.4 g (20 mmol) of 6-fluoro-1,3,4,9-tetrahydropyrano[3,4-b]indole-1,3-dione and of 8.3 ml (100 mmol) of pyrrolidine in 100 ml of dichloromethane is stirred for 24 h at room temperature. The mixture is concentrated under reduced pressure, water is added and the aqueous phase is washed with ethyl acetate. Acidification is carried out with concentrated hydrochloric acid and ethyl acetate is added. The precipitate is collected by filtration, washed with water and dried under reduced pressure. 5 g (17.2 mmol) of solid product are obtained, which product is used as is in the following stage.

11.4. Methyl 5-fluoro-3-(2-oxo-2-(pyrrolidin-1-yl)ethyl)-1H-indole-2-carboxylate.

3.8 ml (51 mmol) of thionyl chloride are added dropwise to a solution of 5 g (17.2 mmol) of 5-fluoro-3-(2-oxo-2-(pyrrolidin-1-yl)ethyl)-1H-indole-2-carboxylic acid in 50 ml of methanol cooled in an ice bath, and then the mixture is heated at reflux for 3 h.

The mixture is concentrated under reduced pressure, water and dichloromethane are added, and the organic phase is washed with water, dried over magnesium sulphate and evaporated under reduced pressure. 4.5 g (14 mmol) df product are obtained, which product is used as is in the following stage.

11.5. Methyl 3-(1-dimethylaminomethylidene-2-oxo-2-(pyrrolidin-1-yl)ethyl)-5-fluoro-1-methyl- 1H-indole-2-carboxylate.

A solution of 3.4 g of methyl 5-fluoro-3-(2-oxo-2-(pyrrolidin-1-yl) ethyl)-1H-indole-2-carboxylate and 4.66 ml (35 mmol) of dimethylformamide dimethyl acetal in 34 ml of N,N-dimethylformamide is heated at reflux for 30 h. The mixture is concentrated under reduced pressure, xylene is added and the solvents are evaporated under reduced pressure. 4 g of residue are obtained, which residue contains approximately 50% of the desired product (according to the proton magnetic resonance spectrum) and is used as is in the following stage.

11.6. 6-Fluoro-9-methyl-2-(5-methyl-1,3,4-thia-diazol-2-yl)-4-(pyrrolidin-1-ylcarbonyl)-2,9-dihydro-1H-pyrido[3,4-b]indol-1-one.

A solution of 4 g of the residue obtained in the preceding stage and 1.04 g (5.5 mmol) of 4-methylbenzenesulphonic acid monohydrate in 40 ml of N,N-dimethylformamide is stirred for 15 min. 0.65 g (6.4 mmol) of 2-amino-5-methyl-1,3,4-thiadiazole is added and the mixture is heated at reflux for 24 h.

The mixture is poured into water and ethyl acetate. The precipitate is collected by filtration, washed with water, dried under reduced pressure and recrystallized from N,N-dimethylformamide. 1 g (2.4 mmol) of product is obtained.

Melting point: 299–301° C.

The chemical structures and the physical properties of a few compounds according to the invention are illustrated in the following table.

TABLE (I)

| No. | X | R₁ | R₂ | NR₃R₄ | 3~4 | M.p. (°C.) |
|---|---|---|---|---|---|---|
| 1 | H | Me | Pr | NHMe | / | 150–152 |
| 2 | H | Me | Pr | NMe₂ | / | 142–144 |
| 3 | H | Pr | Pr | NMe₂ | / | 125–126 |
| 4 | H | Me | PhCH₂ | NEt₂ | / | 107–109 |
| 5 | H | Me | PhCH₂ | NMe₂ | / | 162–163 |
| 6 | H | Pr | PhCH₂ | NMe₂ | / | 178–180 |
| 7 | H | Me | 4-MeO—PhCH₂ | NMe₂ | / | 149–150 |
| 8 | H | Me | 4-F—PhCH₂ | NMe₂ | / | 174 |
| 9 | H | Me | PhCH₂CH₂ | NMe₂ | / | 138–139 |
| 10 | H | Me | 4-Cl—PhCH₂ | NMe₂ | / | 168–170 |
| 11 | H | Et | PhCH₂ | NMe₂ | / | 172–174 |
| 12 | H | Me | 2-MeO—PhCH₂ | NMe₂ | / | 162–163 |
| 13 | H | Me | 3-MeO—PhCH₂ | NMe₂ | / | 139–140 |
| 14 | H | Me | 2-Me—PhCH₂ | NMe₂ | / | 154–156 |
| 15 | H | Me | 3-Me—PhCH₂ | NMe₂ | / | 137–139 |
| 16 | H | Et | 4-MeO—PhCH₂ | NMe₂ | / | 149–150 |
| 17 | H | Me | 4-Me—PhCH₂ | NMe₂ | / | 153–155 |
| 18 | H | Me | Ph(CH₂)₃ | NMe₂ | / | 118–120 |
| 19 | 5-F | Me | PhCH₂ | NMe₂ | / | 195–196 |
| 20 | 6-F | Me | PhCH₂ | NMe₂ | / | 185–186 |
| 21 | 7-F | Me | PhCH₂ | NMe₂ | / | 195–196 |
| 22 | 8-F | Me | PhCH₂ | NMe₂ | / | 188–190 |
| 23 | 6-MeO | Me | PhCH₂ | NMe₂ | / | 181–182 |
| 24 | 7-MeO | Me | PhCH₂ | NMe₂ | / | 208–210 |
| 25 | 6-Cl | Me | PhCH₂ | NMe₂ | / | 208–210 |
| 26 | 7-Cl | Me | PhCH₂ | NMe₂ | / | 209–210 |
| 27 | 8-Cl | Me | PhCH₂ | NMe₂ | / | 218–219 |
| 28 | 6-Me | Me | PhCH₂ | NMe₂ | / | 209–210 |
| 29 | 7-Me | Me | PhCH₂ | NMe₂ | / | 203–205 |
| 30 | 8-Me | Me | PhCH₂ | NMe₂ | / | 204–205 |
| 31 | 6 F | Me | PhCH₂ | NEt₂ | / | 120–121 |
| 32 | 6 F | Me | PhCH₂ | NPr₂ | / | 156–157 |
| 33 | 6-F | Et | 2-MeO—PhCH₂ | NMe₂ | / | 136 137 |
| 34 | 6-F | Me | PhCH₂ | NHMe | / | 205–206 |
| 35 | 6-F | Et | PhCH₂ | NMe₂ | / | 206–207 |
| 36 | 6-Cl | Me | MeO(CH₂)₂ | NMe₂ | / | 217–219 |
| 37 | 6-F | Me | PhCH₂ | NH₂ | / | 259–260 |
| 38 | 6-F | Me | 2-Pyridyl-CH₂ | NMe₂ | / | 186–189 |
| 39 | 6-F | Me | 2-Thienyl-CH₂ | NMe₂ | / | 191–193 |
| 40 | 6-F | Me | 3-Pyridyl-CH₂ | NMe₂ | / | 200–202 |
| 41 | 6-F | Me | C₆H₁₁CH₂ | NMe₂ | / | 209–211 |
| 42 | 6-F | Me | PhCH₂ | Piperid | / | 205 206 |
| 43 | 6-F | Me | PhCH₂ | Pyrrolid | / | 228–229 |
| 44 | H | Pr | Pr | NMe₂ | // | 107–108 |
| 45 | H | Me | PhCH₂ | NMe₂ | // | 130–131 |
| 46 | H | Pr | PhCH₂ | NMe₂ | // | 160–162 |
| 47 | H | Me | 4-MeO—PhCH₂ | NMe₂ | // | 98–100 |
| 48 | H | Me | 4-F—PhCH₂ | NMe₂ | // | 105–106 |
| 49 | H | Me | 4-Cl—PhCH₂ | NMe₂ | // | 103–104 |
| 50 | H | Et | PhCH₂ | NMe₂ | // | 168 170 |
| 51 | H | Me | 2-MeO—PhCH₂ | NMe₂ | // | 171–173 |
| 52 | H | Me | 3-MeO—PhCH₂ | NMe₂ | // | 168–170 |
| 53 | H | Me | 3-Me—PhCH₂ | NMe₂ | // | 117–118 |
| 54 | H | Et | 4-MeO—PhCH₂ | NMe₂ | // | 127–128 |
| 55 | H | Me | 2-Me—PhCH₂ | NMe₂ | // | 157–158 |
| 56 | H | Me | 4-Me—PhCH₂ | NMe₂ | // | 98–100 |
| 57 | H | Me | Ph(CH₂)₃ | NMe₂ | // | 107–109 |
| 58 | 5-F | Me | PhCH₂ | NMe₂ | // | 168–170 |
| 59 | 6 F | Me | PhCH₂ | NMe₂ | // | 192–193 |
| 60 | 7-F | Me | PhCH₂ | NMe₂ | // | 142–144 |
| 61 | 8-F | Me | PhCH₂ | NMe₂ | // | 190–192 |
| 62 | 6-MeO | Me | PhCH₂ | NMe₂ | // | 178–180 |
| 63 | 7-MeO | Me | PhCH₂ | NMe₂ | // | 155–156 |

TABLE-continued (I)

| No. | X | R₁ | R₂ | NR₃R₄ | 3~4 | M.p. (°C.) |
|---|---|---|---|---|---|---|
| 64 | 6-Cl | Me | PhCH₂ | NMe₂ | // | 200–202 |
| 65 | 7-Cl | Me | PhCH₂ | NMe₂ | // | 183–184 |
| 66 | 6-Me | Me | PhCH₂ | NMe₂ | // | 158–160 |
| 67 | 7-Me | Me | PhCH₂ | NMe₂ | // | 154 156 |
| 68 | 8-Me | Me | PhCH₂ | NMe₂ | // | 168–169 |
| 69 | 6-F | Et | PhCH₂ | NMe₂ | // | 216–217 |
| 70 | 6-Cl | Me | MeO—(CH₂)₂ | NMe₂ | // | 179–180 |
| 71 | 6-F | Me | 2-Pyridyl-CH₂ | NMe₂ | // | 221–223 |
| 72 | 6-F | Me | 2-Thienyl-CH₂ | NMe₂ | // | 164–165 |
| 73 | 6-F | Me | C₆H₁₁CH₂ | NMe₂ | // | 170–172 |
| 74 | 6-F | Et | 2-MeO—PhCH₂ | NMe₂ | // | 199–200 |
| 75 | 6-F | Me | 3-Pyridyl-CH₂ | NMe₂ | // | 172–175 |
| 76 | 6-F | Me | PhCH₂ | NMe | / | 204 205 |
| 77 | 6-F | Me | PhCH₂ | NMe₂ | / | 199–202 |
| 78 | H | H | Pr | NHMe | / | 215–217 |
| 79 | H | H | Pr | NMe₂ | / | 202–204 |
| 80 | H | H | Pr | NH₂ | / | 220–222 |
| 81 | H | H | Pr | NHCH₂Ph | / | 228–230 |
| 82 | H | H | Pr | NMe₂ | // | 244–247 |
| 83 | H | H | Ph | NMe₂ | // | 292–294 |
| 84 | 6-F | H | PhCH₂ | NMe₂ | // | 298 301 |
| 85 | 6-F | H | PhCH₂ | NMe₂ | / | 320–322 |
| 86 | 6-F | H | PhCH₂ | NHMe | / | 271–273 |
| 87 | 6-F | H | PhCH₂ | NHMe | // | >300 |
| 88 | H | H | PhCH₂ | NMe₂ | // | 268–269 |
| 89 | 6-F | H | Me | NMe₂ | // | >300 |
| 90 | 6-F | H | iPr | NMe₂ | // | 284–285 |
| 91 | 6-Cl | H | PhCH₂ | NMe₂ | // | >300 |
| 92 | 6-MeO | H | PhCH₂ | NMe₂ | // | >300 |
| 93 | 6-Me | H | PhCH₂ | NMe₂ | // | 267 268 |
| 94 | 6-F | H | Ph | NMe₂ | // | 295–297 d |
| 95 | 6-F | H | Ph | NMe₂ | / | 300 d |
| 96 | 6-F | H | 2-Thienyl-CH₂ | NMe₂ | // | 318–320 |
| 97 | H | Me | Ph | NMe₂ | / | 196–197 |
| 98 | 6-F | Me | Ph | Pyrrolid | // | 203–205 |
| 99 | 6 F | Me | 3-Thienyl-CH₂ | NMe₂ | / | 196–197 |
| 100 | 6-F | Me | 3 Thienyl-CH₂ | NMe₂ | // | 172–174 |
| 101 | 6-F | Me | Ph | NMe₂ | // | 195 197 |
| 102 | 6-F | Me | Ph | NMe₂ | / | 213–215 |
| 103 | 6-F | Et | Ph | NMe₂ | // | 210–212 |
| 104 | 6-F | Me | 2-F—Ph | NMe₂ | // | 235–237 |
| 105 | 6-F | Me | 4-F—Ph | NMe₂ | // | 214–215 |
| 106 | 6-Cl | Me | Ph | NMe₂ | // | 195–196 |
| 107 | 6-F | Me | 4-Me—Ph | NMe₂ | // | 252–254 |
| 108 | 6-Me | Me | Ph | NMe₂ | // | 192–193 |
| 109 | H | Me | Ph | NMe₂ | // | 205–207 |
| 110 | 6 F | Me | Ph | NHCH₂Ph | // | 243–244 |
| 111 | 6-F | Me | Ph | NHMe | // | 294–296 |
| 112 | 6-F | Me | 3-F—Ph | NMe₂ | // | 199–202 |
| 113 | 6-F | Me | 3-Cl—Ph | NMe₂ | // | 186–188 |
| 114 | 6-F | Me | 3-MeO—Ph | NMe₂ | // | 215 |
| 115 | 6-F | Me | Ph | Morph | // | 254–255 |
| 116 | 6-F | Me | Ph | 4 Me-piperaz | // | 224–226 |
| 117 | 6 F | Me | Ph | Piperid | // | 178–180 |
| 118 | 6 F | Me | Ph | NEt₂ | // | 164 165 |
| 119 | 6-F | Me | Ph | N(Me)(CH₂)₂OMe | // | 172–174 |
| 120 | 6-F | Me | Ph | 3-HO-pyrrolid | // | 201–202 |
| 121 | 6-F | Me | Ph | 3-EtO-pyrrolid | // | 189–190 |
| 122 | 6-F | Me | 2-Pyridyl | NMe₂ | // | 220–221 |
| 123 | 6-F | Me | Ph | N(Me)Et | // | 181–182 |
| 124 | 6-F | Me | Ph | Pyrrolid | // | 203–205 |
| 125 | 6-F | Me | 5-Me-thiadiaz | Pyrrolid | // | 299–301 |
| 126 | 6-F | Et | Ph | Pyrrolid | // | 172–174 |

TABLE-continued (I)

| No. | X | $R_1$ | $R_2$ | $NR_3R_4$ | 3 ~ 4 | M.p. (° C.) |
|---|---|---|---|---|---|---|
| 127 | 6 Cl | Me | Ph | Pyrrolid | // | 209–210 |
| 128 | 6-F | Me | 5-Me-oxazol | Pyrrolid | // | 248–250 |
| 129 | 6-F | Me | Ph | Azetid | // | 230–231 |
| 130 | 6-F | Me | Ph | N(Me)Pr | // | 172–173 |
| 131 | 6-F | PhCH$_2$ | Ph | NMe$_2$ | // | 201–203 |
| 132 | 6-F | Me | Ph | N(Me)CH$_2$Ph | // | 148–149 |
| 133 | 6-F | cPrCH$_2$ | Ph | NMe$_2$ | // | 178–179 |
| 134 | 6-F | Me | 1-Napht | NMe$_2$ | // | 245–247 |
| 135 | 6 F | Me | 2-Napht | NMe$_2$ | // | 185–186 |
| 136 | 6-F | Me | Ph | (S)-2-MeOCH$_2$— pyrrolid | // | 96–107 |
| 137 | 6-F | Me | Ph | N(Me)CH$_2$CH$_2$Ph | // | 174–176 |
| 138 | 6-F | Me | Ph | N(Me)CH$_2$CO$_2$Et | // | 158–160 |
| 139 | 6-F | Me | Ph | 2-MeOCO— pyrrolid | // | 115–118 |
| 140 | 6-F | Me | Ph | N(Me)CH$_2$CH$_2$Ph | // | 151–153 |
| 141 | 6-F | Me | Ph | Thiazolid | // | 187–188 |
| 142 | 6-MeO | Me | Ph | Pyrrolid | // | 258–259 |
| 143 | 6 F | Et | Ph | N(Me)Et | // | 174–175 |
| 144 | 6-OCH$_2$Ph | Me | Ph | Pyrrolid | // | 199–201 |
| 145 | 6-CF$_3$ | Me | Ph | Pyrrolid | // | 211–212 |
| 146 | 6-F | H | Ph | Pyrrolid | // | 283–285 |
| 147 | 6-F | Me | Ph | NH(CH$_2$)$_4$OH | // | 210–213 |
| 148 | 6-F | Me | Ph | NH(CH$_2$)$_3$CO$_2$H | // | 278–279 |
| 149 | 6-F | Me | Ph | NH(CH$_2$)$_3$CO$_2$Me | // | 154–156 |

Key
Me denotes a methyl group, Et denotes an ethyl group, Pr denotes a propyl group, iPr denotes an isopropyl group, cPr denotes a cyclopropyl group, Ph denotes a phenyl group, 1-Napht and 2-Napht respectively denote naphth-1-yl and naphth-2-yl groups, x-Pyridyl denotes a pyridin-x-yl group, x-Thienyl denotes a thien-x-yl group, Piperid denotes a piperidin-1-yl group, Pyrrolid denotes a pyrrolidin-1-yl group, Morph denotes a morpholin-4-yl group, Azetid denotes an azetidin-1-yl group, 4-Me-piperaz denotes a 4-methylpiperazin-1-yl group, 5-Me-thiadiaz denotes a 5-methyl-1,3,4-thiadiazol-2-yl group, 5-Me-oxazol denotes a 5-methyl-1,2-oxazol-2-yl group, and Thiazolid denotes a thiazolidinyl group.
In the column "3 ~ 4", "/" denotes a carbon-carbon single bond and "//" denotes a carbon-carbon double bond between the 3 and 4 atoms of the molecule.
In the "M.p. (° C.)" column, "d" denotes a melting point with decomposition.

The compounds of the invention were subjected to pharmacological tests which demonstrated their advantage as substances having therapeutic activities.
Study of Membrane Binding with Respect to $\omega_1$ (Type 1 Benzodiazepine) and $\omega_2$ (type 2 benzodiazepine) receptors.

The affinity of the compounds for the $\omega_1$ receptors of the cerebellum and $\omega_2$ receptors of the spinal cord was determined according to a variant of the method described by S. Z. Langer and S. Arbilla in *Fund. Cdin. Pharmacol.*, 2, 159–170 (1988), with the use of [$^3$H]flumazenil instead of [$^3$H]diazepam as radioligand.

The cerebellar or spinal cord tissue is homogenized for 60 s in 120 or 30 volumes, respectively, of ice-cold buffer (50 mM Tris-HCl, pH 7.4, 120 mM NaCl, 5 mM KCl) and then, after dilution to ⅓, the suspension is incubated with [$^3$H] flumazenil (specific activity 78 Ci/mmol, New England Nuclear) at a concentration of 1 nM and with the compounds of the invention at different concentrations, in a final volume of 525 μl. After 30 minutes of incubation at 0° C., the samples are filtered under reduced pressure on Whatman GF/B® filters and washed immediately with ice-cold buffer.

The specific binding of [$^3$H]flumazenil is determined in the presence of 1 μM unlabelled diazepam. The data are analysed according to standard methods and the IC$_{50}$ concentration, the concentration which inhibits by 50% the binding of [$^3$H]flumazenil, is calculated.

The IC$_{50}$ values of the most active compounds of the invention lie, in this test, between 10 and 1000 nM.
Study of the Anxiolvtic Activity: Drink Intake Conflict Test.

The anxiolytic activity is evaluated in rats in the drink intake conflict test according to the method described by J. R. Vogel, B. Beer and D. E. Clody in *Psychopharmacologia* (Berl.), 21, 1–7 (1971). After being deprived of water for 48 h, the rat is placed in a soundproof chamber equipped with a water pipette connected to an anxiometer which delivers a mild electric shock every 20 licks. The number of shocks received is automatically counted over 3 minutes and makes it possible to evaluate the anxiolytic activity of the tested compounds. The results are expressed by the minimum effective dose (MED), the dose which produces a significant increase in the number of shocks received, with respect to the number observed in the control animals.

The MED values of the most active compounds lie, in this test, between 5 and 50 mg/kg via the intraperitoneal route.

Studs of the Anxiolvtic Activity: Test in a Heightened Cross-shaped Maze

The protocol of this test is a modification of that described by S. Pellow and S. File in *Pharmacol. Biochem. Behav.* (1986), 24, 525–529. After a period of accustomization to the experimental room lasting approximately 24 h, the rats are placed individually on the central platform, the muzzle directed towards one of the closed arms, and observed for 4 min using a video camera. The time spent by the animal in the open arms, the number of entries into the closed arms and into the open arms, the number of attempts to enter the open arms, followed by an avoidance response, and the exploration of the edges in the open arms are recorded. The results are expressed for each animal: 1) as percentage of passages into the open arms relative to the total number of entries into the four arms of the apparatus, 2) as percentage of time spent in the open arms relative to the total duration of the test (4 min), 3) as total number of abortive attempts made by the animal, 4) as total number of explorations.

The products under study are administered intraperitoneally or orally at increasing doses. The results are expressed by the minimum effective dose (MED) which produces either a significant increase (activity in the open arms) or a significant decrease (attempts) relative to the performance observed in the control animals.

The MED values of the most active compounds lie, in this test, between 3 and 50 mg/kg via the intraperitoneal or oral route.

Study of the Hypnotic Activity.

The sedative or hypnotic activity of the compounds was determined by observing their action on the rat's electrocorticogram, according to the method described by H. Depoortere, Rev. E. E. G. *Neurophysiol.*, 10, 3, 207–214 (1980) and by H. Depoortere and M. Decobert, *J. Phaxmacol.*, (Paris), 14, 2, 195–265 (1983).

The products under study were administered intraperitoneally at increasing doses. They induce sleep patterns at doses ranging from 1 to 30 mg/kg.

Study of the Anticonvulsant Activity: Activity with Respect to Clonic Convulsions Induced in Rats by Injection of Pentetrazol.

The protocol of this test is a modification of that described by E. A. Swinyard and J. H. Woodhead in *Antiepileptic Drugs*, Raven Press, New York, 111–126 (1982).

The test products are administered to the animals intraperitoneally 30 min before an intravenous injection of 20 mg/kg of pentetrazol. Immediately after the injection, the number of animals exhibiting clonic convulsions is noted over 5 min.

The results are expressed as the $AD_{50}$, the dose which protects 50% of the animals, calculated according to the method of J. T. Lichtfield and F. Wilcoxon (*J. Pharm. Exp. Ther.* (1949), 96, 99–113) on the basis of 3 or 4 doses each administered to a group of 8 to 10 rats.

The $AD_{50}$ values of the most active compounds lie between 0.3 and 30 mg/kg via the intraperitoneal or oral route.

Study of the Anticonvulsant Activity: Activity with Respect to Isoniazid-induced Convulsions in Mice.

The intrinsic activity of the compounds is determined by the latency time of onset of convulsions induced by the subcutaneous administration of isoniazid (800 mg/kg) simultaneously with the test compound injected intraperitoneally, according to the protocol described by G. Perrault, E. Morel, D. Sanger and B. Zivkovic in *Eur. J. Pharmacol.*, 156, 189–196 (1988) The results are expressed as the $AD_{50}$, the dose which produces 50% of the maximum effect, relative to the control animals, determined on the basis of 3 or 4 doses each administered to a group of 8 to 10 mice. The $AD_{50}$ values of the compounds of the invention lie, in this test, between 1 and 50 mg/kg via the intraperitoneal route and, depending on the compounds, the maximum effect can be as much as 300%.

The results of the tests performed on the compounds of the invention show that, in vitro, they displace [$^3$H] flumazenil from its specific binding sites in the cerebellum and the spinal cord; they exhibit a mixed affinity for the $\omega_1$ and $\omega_2$ (type 1 and type 2 benzodiazepine) sites situated in the $GAB_A$—$\omega$ sites—chlorine channel macromolecular complex.

In vivo, they behave as full or partial agonists with respect to these receptors.

They possess anxiolytic, hypnotic and anticonvulsant properties, and can consequently be used for the treatment of complaints associated with disorders of GABAergic transmission, such as anxiety, sleep disorders, epilepsy, spasticity, muscle contractures, cognitive disorders, withdrawal disorders related to alcoholism, tobacco or drugs, and the like.

They can also be used for the treatment of Parkinson's disease and all types of extrapyramidal syndromes. Finally, they can be used in premedication and as general anaesthetics for the induction and/or maintenance of anaesthesia, or as local anaesthetics, optionally in combination with other anaesthetics and/or muscle relaxants and/or analgesics.

To this end, they may be presented in any pharmaceutical dosage form, in combination with suitable excipients, for enteral or parenteral administration, for example in the form of tablets, dragees, capsules including hard gelatin capsules, solutions or suspensions to be swallowed or injected, suppositories, and the like, containing a dose to permit a daily administration of 1 to 1000 mg of active substance.

We claim:

1. A compound having general formula (I)

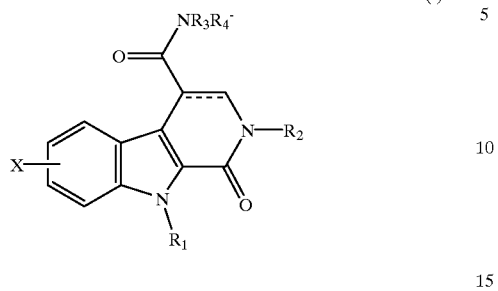

in which
- X represents a hydrogen or halogen atom or a $(C_1-C_3)$ alkyl, $(C_1-C_3)$alkoxy, trifluoromethyl or phenylmethoxy group,
- $R_1$ represents a hydrogen atom or a $(C_1-C_3)$alkyl, cyclopropyl or phenylmethyl group,
- $R_2$ represents either a $(C_1-C_3)$alkyl group optionally substituted by a methoxy group, or a phenyl$(C_1-C_3)$alkyl group optionally substituted on the phenyl ring by a halogen atom or a methyl or methoxy group, or a cyclohexylmethyl group, or a thienylmethyl group, or a pyridinylmethyl group, or a phenyl group optionally substituted by one or more halogen atoms or a $(C_1-C_3)$ alkyl or $(C_1-C_3)$alkoxy group, or a pyridinyl group, or a 5-methyl-1,2-oxazolyl group, or a 5-methyl-1,3,4-thiadiazolyl group, or a naphthyl group,
- $R_3$ and $R_4$, independently of one another, each represent a hydrogen atom, a $(C_1-C_3)$alkyl group, a 2-methoxyethyl group, a hydroxy$(C_2-C_4)$ alkyl group, a carboxy-$(C_1-C_3)$alkyl group, a $(C_1-C_3)$ alkoxycarbonyl$(C_1-C_3)$alkyl group or a phenyl$(C_1-C_3)$ alkyl group, or else together form, with the nitrogen atom which carries them, either a pyrrolidinyl group optionally substituted by a hydroxyl, ethoxy, methoxycarbonyl or methoxymethyl group, or a piperidinyl group, or a morpholinyl group, or a 4-methylpiperazinyl group, or an azetidinyl group, or a thiazolidinyl group, and the bond between the carbon atoms in the 3 and 4 positions is single or double.

2. A compound according to claim 1, wherein, X is in the 6 position and represents a fluorine atom.

3. A compound according to claim 1, wherein $R_1$ represents a methyl group.

4. A compound according to claim 1, wherein $R_2$ represents a phenyl group.

5. A compound according to claim 1, wherein $R_3$ represents a methyl group and $R_4$ represents an ethyl group.

6. A compound according to claim 1, wherein $R_3$ and $R_4$ form, with the nitrogen atom which carries them, a pyrrolidinyl ring.

7. A compound according to claim 1, wherein the compound is in the form of a pure optical isomer.

8. A compound according to claim 1, wherein the compound is in the form of a mixture of optical isomers.

9. A pharmaceutical composition, comprising a compound according to one of claims 1 to 6, in combination with an excipient.

10. A process for the preparation of a compound according to claim 1, which comprises:

(a) reacting a compound of general formula (II)

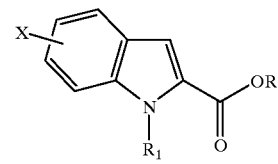

in which X and $R_1$ are as defined in claim 1 and R represents a $(C_1-C_3)$alkyl group, with ethyl pyruvate, to obtain a diester of general formula (IV)

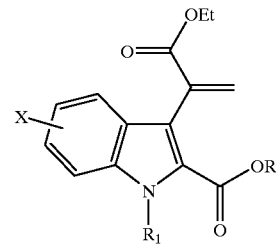

(b) treating said diester with an amine of general formula $R_2NH_2$, in which $R_2$ is as defined in claim 1, to obtain an ester of general formula (V)

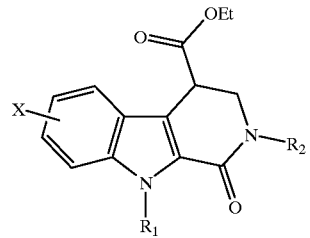

(c) converting said ester by hydrolysis to a corresponding acid, of general formula (VI)

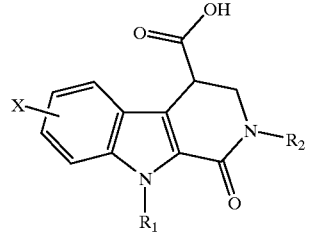

and (d) converting said acid, by reaction with an amine of general formula $HNR_3R_4$, in which $R_3$ and $R_4$ are as defined in claim 1, either through an imidazolide obtained by reaction with N,N-carbonyldiimidazole or through an acid chloride, to a primary, secondary or tertiary amide of general formula (I')

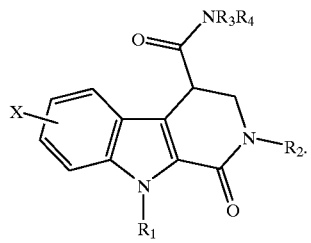

(I')

11. A process as claimed in claim 10, which further comprises oxidizing said primary, secondary or tertiary amide of general formula (I') by means of 2,3-dichloro-5,6-dicyanocyclohexa-2,5-diene-1,4-dione or of 3,4,5,6-tetrachlorocylohexa-3,5-diene-1,2-dione to obtain a corresponding compound of general formula (I")

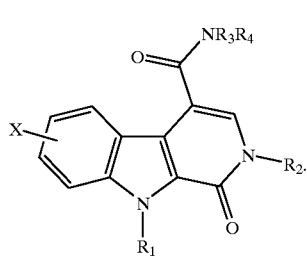

(I")

12. A process for the preparation of a compound according to claim 1, which comprises:

(a) reacting a compound of general formula (VII)

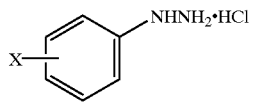

(VIII)

in which X is as defined in claim 1, with 2-ketoglutaric acid;

(b) treating the product of step (a) in an acidic alcoholic medium to obtain a diester of general formula (IX)

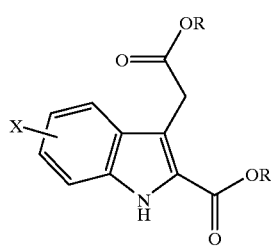

(IX)

in which R represents a $(C_1-C_3)$alkyl group;

(c) alkylating the diester of formula (IX) to obtain a compound of general formula (X)

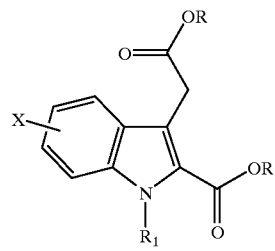

(X)

in which $R_1$ represents a $(C_1-C_3)$alkyl group;

(d) converting said compound of general formula (X), in the presence of dimethylformamide dimethyl acetal, into a compound of general formula (XI)

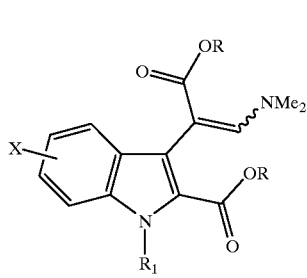

(XI)

in which $R_1$ represents a methyl group;

(e) treating said compound of general formula (XI) with an amine of general formula $H_2NR_2$, in which $R_2$ is as defined in claim 1, to obtain an ester of general formula (V')

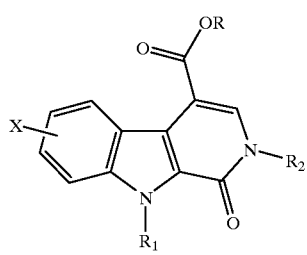

(V')

(f) converting said ester to a corresponding acid of general formula (VI')

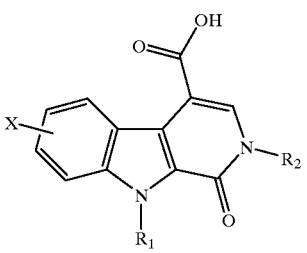

(VI')

and (g) converting said acid to a primary, secondary or tertiary amide of general formula (I")

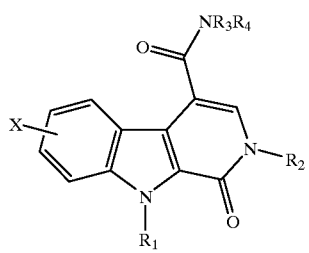
(I")

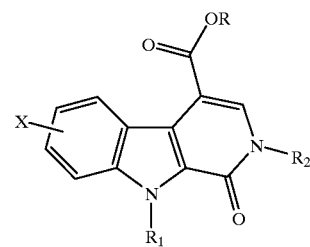
(V')

either through an imidazolide obtained by reaction with N,N'-carbonyldiimidazole or through an acid chloride.

13. A process for the preparation of a compound according to claim 1, which comprises:

(a) reacting a compound of general formula (VIII)

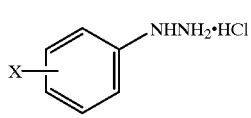
(VIII)

in which X is as defined in claim 1, with 2-ketoglutaric acid;

(b) treating the product of step (a) in an acidic alcoholic medium to obtain a diester of general formula (IX)

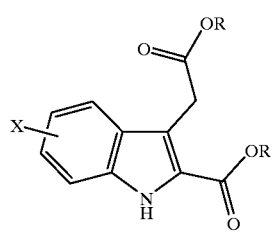
(IX)

in which R represents a $(C_1-C_3)$alkyl group;

(c) converting said diester of formula (IX) directly into a compound of general formula (XI)

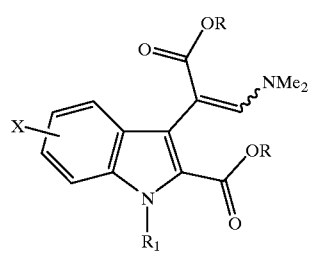
(XI)

in which $R_1$ represents a methyl group;

(d) treating said compound of general formula (XI) with an amine of general formula $H_2NR_2$, in which $R_2$ is as defined in claim 1, to obtain an ester of general formula (V')

(e) converting said ester to a corresponding acid of general formula (VI')

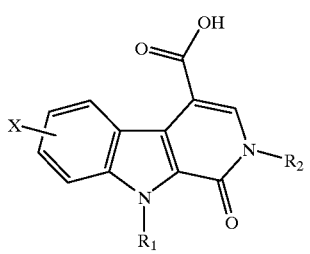
(VI')

and (f) converting said acid to a primary, secondary or tertiary amide of general formula (I")

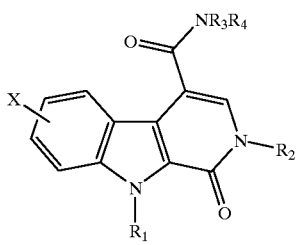
(I")

either through an imidazolide obtained by reaction with N,N'-carbonyldiimidazole or through an acid chloride.

14. A process for the preparation of a compound according to claim 1, which comprises:

(a) hydrolyzing a diester of general formula (X)

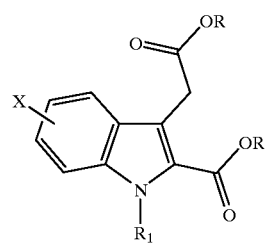
(X)

in which X and $R_1$ are as described in claim 1, to obtain a diacid of general formula (XII)

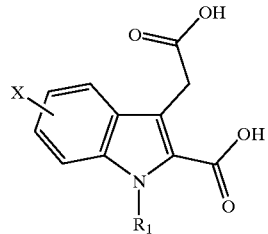
(XII)

(b) converting said diacid to an anhydride, to obtain a compound

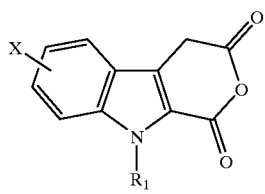
(XIII)

of the general formula (XIII)

(c) reacting said anhydride with an amine of general formula $HNR_3R_4$, in which $R_3$ and $R_4$ are as defined in claim 1, to obtain a compound of general formula (XIV)

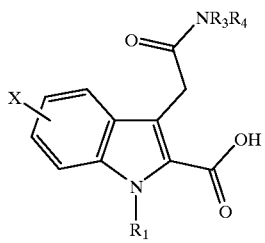
(XIV)

(d) converting said compound of general formula (XIV) to an ester of general formula (XV)

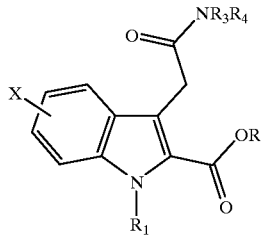
(XV)

(e) treating said ester in the presence of dimethylformamide dimethyl acetal, to obtain a compound of general formula (XVI)

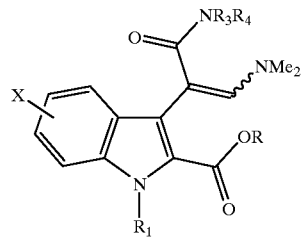
(XVI)

and (f) reacting said compound of general formula (XVI) with an amine of general formula $R_2NH_2$, in which $R_2$ is as defined in claim 1, to obtain a compound of general formula (I″)

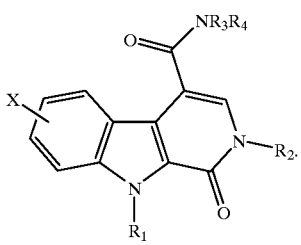
(I″)

15. A process as claimed in claim 14, further comprising, when the compound of general formula (I″) is a secondary amide, converting said secondary amide to a tertiary amide by an alkylation reaction.

* * * * *

UNITED STATES PATENT AND TRADEMARK OFFICE
CERTIFICATE OF CORRECTION

PATENT NO. : 6,075,021
DATED : June 13, 2000
INVENTOR(S) : Yannic, Evanno et al.

Page 1 of 1

It is certified that error appears in the above-identified patent and that said Letters Patent is hereby corrected as shown below:

Column 29, claim 9,
Line 63, after "composition" insert -- of claim 1 --.
Line 64, delete "according to one of claims 1 to 6".

Column 30, claim 10,
Line 65, insert " ' " (prime) after second "N".

Column 31, claim 12,
Line 37, "(VII)" should read -- (VIII) --.

Signed and Sealed this

Ninth Day of April, 2002

Attest:

Attesting Officer

JAMES E. ROGAN
Director of the United States Patent and Trademark Office